United States Patent
Della Ciana

(10) Patent No.: US 8,129,136 B2
(45) Date of Patent: Mar. 6, 2012

(54) KIT FOR PERFORMING AN ASSAY

(75) Inventor: Leopoldo Della Ciana, Bologna (IT)

(73) Assignee: Cyanagen Srl, Bologna (IT)

( * ) Notice: Subject to any disclaimer, the term of this patent is extended or adjusted under 35 U.S.C. 154(b) by 0 days.

(21) Appl. No.: 12/805,827

(22) Filed: Aug. 20, 2010

(65) Prior Publication Data

US 2011/0053200 A1 Mar. 3, 2011

Related U.S. Application Data

(63) Continuation of application No. 12/071,333, filed on Feb. 20, 2008, now Pat. No. 7,803,573.

(30) Foreign Application Priority Data

Feb. 20, 2007 (IT) .................................. BO07A0112

(51) Int. Cl.
*C12Q 1/28* (2006.01)
(52) U.S. Cl. .......................................... 435/28; 435/975
(58) Field of Classification Search .................... 435/28, 435/975
See application file for complete search history.

(56) References Cited

U.S. PATENT DOCUMENTS

| | | | |
|---|---|---|---|
| 4,279,950 A | 7/1981 | Tanaka et al. | |
| 4,950,588 A | 8/1990 | Dattagupta | |
| 5,171,668 A | 12/1992 | Sugiyama | |
| 5,206,149 A | 4/1993 | Oyama et al. | |
| 5,556,758 A | 9/1996 | Allen | |
| 5,629,168 A | 5/1997 | Kricka | |
| 5,686,258 A | 11/1997 | Akhavan-Tafti et al. | |
| 6,852,503 B1 | 2/2005 | Clothier | |
| 7,563,902 B2 | 7/2009 | Heindl et al. | |
| 7,803,573 B2 * | 9/2010 | Della Ciana | 435/28 |
| 2005/0106652 A1 | 5/2005 | Massey et al. | |

FOREIGN PATENT DOCUMENTS

| | | |
|---|---|---|
| EP | 0 603 953 A1 | 6/1994 |
| JP | 07099996 | 4/1995 |

OTHER PUBLICATIONS

Jonsson T. et al. New Nucleophilic Catalysts for Bright and Fast Peroxyoxalate Chemiluminescence. Analytical Chemistry 72(7)1373-1380, Apr. 2000.*
European Search Report issued May 23, 2008.
Jonsson, T., et al, Analytica Chimica Acta, vol. 400, (1999) 257-264; "Very fast peroxyoxalate chemiluminescence;" XP-002478244.
Jonsson, T., et al, Analytical Chemistry, vol. 72, No. 7, Apr. 1, 2000, 1373-1380, "New Nucleophilic Catalysts for Bright nd Fast Peroxyoxalate Chemiluminescence," XP-002478245.
Hofmann, O., et al, Sensors and Actuators B-106 (2005) 878-884, "Thin-film organic photodiodes as integrated detectors for microscale chemiluminescence assays," XP004867952.
Kricka, L.J., Clinical Chemistry, 37/9, 1472-1481 (1991), "Chemiluminescent and Bioluminescent Techniques."
Vlasenko, S.B., et al, Journal of Bioluminescence and Chemiluminescence, vol. 4, 164-176 (1989).
Cercek, D., et al, J. Biolumin. Chemilumin., 1994; 9: 273-277 (Abstract) "Effect of oxygen abstraction on the peroxidase-luminol-perborate system: Relevance to the HRP enhanced chemiluminescence mechanism."
Merenyi, G., et al, J. Am. Chem. Soc, 1986, 108: 7716-7726, "Nucleophilic Addition to Diazaquinones. Formation and Breakdown of Tetrahedral Intermediates in Relation to Luminol Chemiluminescence."
Scriven, E.F.V., Chem. Soc. Rev. 1983, 12:129-161, "4-Dialkylaminopyridines: Super Acylation and Alkylation Catalysts."
Hassner, A., et al, Tetrahedron, vol. 34, pp. 2069-2076, "Aminopyridines as Acylation Catalysts for Tertiary Alcohols.", (14) 1978.
Hofle, G., et al, Angew. Chem. Int. Ed. Engl., 17:569-583 (1978), "4-Dialkylaminopyridines as Highly Active Acylation Catalysts."
Kricka, L.J., et al, Methods Enzymol. 2000; 305:370-390, "Chemiluminescent Methods for Detecting and Quantitating Enzyme Activity."
Kricka, L.J., et al, Anal. Biochem . 1996; 240:119-125, "Synthesis and Characterization of 4-iodophenylboronic Acid: A New Enhancer for the Horseradish Peroxidase Chemiluminescent-Catalyzed Oxidation of Luminol."
Thorpe, G.H.G., et al, Enhanced Chemiluminescence, 1986, 33: 331-353, "Enhanced Chemiluminescent Reactions Catalyzed by Horseradish Peroxidase."
Marzocchi et al, "Chemiluminescent detection systems of horseradish peroxidase employing nucleophilic acylation catalysts", Analytical Biochemistry 377:189-194 (2008).
Hofmann et al, "Thin-film organic photodiodes as integrated detectors for microscale chemiluminescence assays", Sensors and Actuators B 106:878-884 (2005).
Jonsson et al, "New Nucleophilic Catalysts for Bright and Fast Peroxyoxalate Chemiluminescence", Anal. Chem. 72(7):1373-1380 (2000).
Office Action dated Dec. 11, 2009 issued in connection with U.S. Appl. No. 12/071,333.
European Search Report issued Apr. 25, 2008 in EP 08151414.
Hassner et al, "Aminopyridines As Acylation Catalysts for Tertiary Alcohols", Tetrahedron 34:2069-2076 (1978).

* cited by examiner

*Primary Examiner* — Ralph Gitomer
(74) *Attorney, Agent, or Firm* — Nixon & Vanderhye P.C.

(57) ABSTRACT

The present invention relates to a kit for performing an assay. The kit comprises luminol, an oxidant, an electron mediator and a hypernucleophilic acylation catalyst.

11 Claims, 4 Drawing Sheets

KIT FOR PERFORMING AN ASSAY

This application is a continuation of U.S. application Ser. No. 12/071,333, filed Feb. 20, 2008, now U.S. Pat. No. 7,803,573, which claims priority from IT Application No. BO2007A000112, filed Feb. 20, 2007, the entire content of which is hereby incorporated by reference.

FIELD OF THE INVENTION

The present invention concerns a new method for increasing light emission generated by the chemiluminescent reaction of luminol, a peroxydase enzyme, an oxidant and an electron mediator.

BACKGROUND ART

The chemiluminescent reaction is that between luminol, a peroxide source and a peroxydase enzyme, especially horseradish peroxidase (HRP), that catalyzes the oxidation of luminol by peroxide. Such oxidation is accompanied by light emission.

The chemiluminescent oxidation of luminol catalyzed by peroxidase finds wide employment in analytical tests of antigens, antibodies and nucleic acids, and in particular in blotting tests, e.g., Dot Blots, Western Blots (proteins), Southern and the Northern Blots (nucleic acids).

It is known that the chemiluminescent oxidation of luminol catalyzed by peroxidase can be made faster and more efficient by adding an electron mediator, or enhancer, as shown, for example, by L. J. Kricka in Clinical Chemistry 1991; 37:1472-1481; or by L. J. Kricka, J. C. Voyta and I. Bronstein in "Chemiluminescent Methods for Detecting and Quantitating Enzyme Activity", Methods Enzymol. 2000; 305:370-390. Several compounds have been used as electron mediators. In particular, firefly luciferin, 6-hydroxybenzotriazole, p-iodophenol, p-coumaric acid are described by G. H. G. Thorpe and L. J. Kricka, Methods Enzymol. 1986; 133:331; aromatic amines in U.S. Pat. No. 4,279,950; acetanilides in Eur. Pat. Appl. No. 603953 (1994); the indophenols and phenothiazines N-substituted and indophenols in U.S. Pat. No. 5,171,668; boronic acids replaced in U.S. Pat. No. 5,629,168. It is believed that in the presence of an electron mediator, the oxidation of luminol catalyzed by peroxidase proceeds as follows:

$$HRP + H_2O_2 \rightarrow HRP\text{-}I \quad (1)$$

$$HRP\text{-}I + LH^- \rightarrow HRP\text{-}II + L^{\cdot-} \quad (2)$$

$$HRP\text{-}II + LH^- \rightarrow HRP + L^{\cdot-} \quad (3)$$

$$HRP\text{-}I + E \rightarrow HRP\text{-}II + E^{\cdot} \quad (4)$$

$$HRP\text{-}II + E \rightarrow HRP + E^{\cdot} \quad (5)$$

$$E^{\cdot} + LH^- \rightarrow E + L^{\cdot-} \quad (6)$$

$$L^{\cdot-} \rightarrow L + LH^- \quad (7)$$

$$L + H_2O_2 \rightarrow LO_2^{2-} \quad (8)$$

$$LO_2^{2-} \rightarrow (AP^{2-})^* + N_2 \quad (9)$$

$$(AP^{2-})^* \rightarrow AP^{2-} + h\nu \quad (10)$$

where HRP, HRP-I and HRP-II indicate the enzyme peroxidase in the native form and in its two oxidized forms, respectively; $LH^-$, $LH^{\cdot-}$, $L$, $LO_2^{2-}$ represent luminol anion, luminol radical anion, diazaquinone and luminol peroxide; E ed $E^{\cdot}$ represent the electron mediator and its corresponding radical; finally, $AP^{2-}$ indicates the dianion of 3-aminophthalic acid, and $(AP^{2-})^*$ its excited state. According to this scheme, peroxidase HRP is oxidized by peroxide to HRP-I. The luminol anion and the enhancer are oxidized by HRP-I to their respective radicals with conversion of the enzyme to its HRP-II form. In turn, HRP-II oxidizes another molecule of luminol anion or of electron mediator to their respective radicals, simultaneously regenerating the native form of the HRP enzyme, which can participate in another oxidation cycle. It is thus believed that the increase in the chemiluminescent signal is due to the faster generation of the key intermediate $LH^{\cdot-}$ in the presence of an electron mediator (see e.g., S. B. Vlasenko, A. A. Arefyev, A. D. Klimov, B. B. Kim, E. L. Gorovits, A. P. Osipov, E. M. Gavrilova, A. M. Yegorov, J. Biolumin. Chemilumin. 1989; 4:164-176, or B. Cercek, K. Roby, L. Cercek, J. Biolumin. Chemilumin. 1994; 9:273-277).

The subsequent phases of the chemiluminescent reaction are less clear. The radical anion of luminol $LH^{\cdot-}$ is unstable and can dismutate to luminol anion $LH^-$ and diazaquinone, L. The diazaquinone in turn is likely to be susceptible to nucleophilic attack by peroxide ion $HO_2^-$ on the carbonylic carbon (C=O), with formation of luminol peroxide $LO_2^{2-}$, in the open or cyclical form (endoperoxide). Finally, luminol peroxide collapses to 3-aminophthalate, $AP^{2-}$, with expulsion of molecular nitrogen. Some of the energy thus produced is captured by aminophthalate with formation of its excited state $(AP^{2-})^*$ and subsequent emission of blue light (425 nm). The efficiency of this process corresponds to the fluorescence quantum yield of 3-aminophthalate (approximately 30%). Although the exact details of reactions (7)-(9) are not known, it is conceivable that the conversion of luminol radical anion, $LH^{\cdot-}$, to luminol peroxide, $LO_2^{2-}$, involves nucleophilic attack of peroxide ion on a carbonylic carbon (C=O) of luminol (see e.g., G. Merenyi, J. Lind and T. E. Eriksen "Nucleophilic Addition to Diazaquinones. Formation and Breakdown of Tetrahedral Intermediates in relation to Luminol Chemiluminescence," J. Am. Chem. Soc. 1986; 108:7716-7726.) On the other hand, the efficiency of this reaction is decisive for the formation of $(AP^{2-})^*$.

OBJECT AND SUMMARY OF THE INVENTION

Object of the present invention is to provide a new method for increasing light emission generated by the chemiluminescent reaction of luminol, a peroxydase enzyme, an oxidant and an electron mediator.

According to the invention, the above object is achieved thanks to the solution recalled specifically in the ensuing claims, which are understood as forming an integral part of the present description.

In an embodiment, this invention provides for the use, in chemiluminescent compositions, of a hypernucleophilic acylation catalyst (HNAC) belonging to the class of 4-aminopyridines and particularly compounds defined by the following formula (I):

FORMULA (I)

where:
$R_1$ and $R_2$ represent both or each separately, hydrogen, methyl, ethyl, propyl, butyl and isopropyl,
or
$R_1$ and $R_2$ together represent —$(CH_2)_4$— thus forming a pyrrolidone ring with the nitrogen atom,
or
$R_1$ and $R_2$ together represent —$(CH_2)_5$— thus forming a piperidine ring with the nitrogen atom,
or
$R_1$ and $R_2$ together represent —$(CH_2)_2$—$CHCH_3$—$(CH_2)_2$— thus forming a 4-methylpiperidine ring with the nitrogen atom,
or
$R_1$ and $R_2$ together represent —$(CH_2)_2$—O—$(CH_2)_2$— thus forming a morpholine ring with the nitrogen atom,
or
$R_1$ and $R_2$ together represent —$(CHCH_3)$—CH=CH$(CHCH_3)$— thus forming a 2,5-dimethyl-2,5-dihydro-1H-pyrrole ring with the nitrogen atom.

In an embodiment, this invention provides for the use, in chemiluminescent compositions, of a hypernucleophilic acylation catalyst (HNAC) belonging to the class of 4-aminopyridines and particularly compounds defined by the following formula (II):

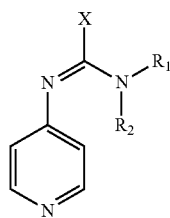

FORMULA (II)

where:
X represents hydrogen, methyl, ethyl, propyl, butyl or isopropyl, while $R_1$ and $R_2$ represent both or each separately, hydrogen, methyl, ethyl, propyl, butyl and isopropyl,
or
X represents $NH_2$, or $N(methyl)_2$, or $N\,ethyl)_2$, or $N(propyl)_2$, or $N(isopropyl)_2$, or $N(butyl)_2$, while $R_1$ and $R_2$ represent both or each separately, hydrogen, methyl, ethyl, propyl, isopropyl, or butyl.

Although the present invention concerns the use, in general and for whatever purpose, of hypernucleophilic acylation catalyst to increase light emission produced by the chemiluminescent reaction, it is, however, primarily applicable in the context of an assay.

The term "assay" means the detection, semiquantification and quantification of an analyte. Typically the implementation of an assay requires to relate the light output to the amount of peroxidase used, so that peroxidase is the substance determined directly. Although the present invention is useful for determining the presence or amount of any of the reaction partners (luminol; peroxidase; oxidant; mediator of electrons; hypernucleophilic acylation catalyst), the reaction partner is not necessarily the substance itself to be determined. For example, the oxidant can be produced by a previous reaction, or a series of previous reactions.

Peroxidase or luminol may be present in the form of a conjugated antibody used in an immunoenzymatic assay to determine an antigen. Or peroxidase or luminol may be conjugated to a nucleotide, an oligonucleotide or a nucleic acid in hybridisation assays. Therefore, the present invention is applicable to any method of diagnostic assay of a substance whose presence or amount is related to the presence or amount of a partner reaction selected from the group consisting of luminol, a peroxidase enzyme, an oxidant, an enhancer and a hypernucleophilic acylation catalyst that co-react in a chemiluminescent reaction, whose emission of light is detected or measured so that the presence or amount of material to be analysed is related to the production of light. The present invention also includes a kit for performing an assay comprising luminol, an oxidant, a electron mediator and a hypernucleophilic acylation catalyst.

BRIEF DESCRIPTION OF THE DRAWINGS

The invention will now be described, by way of example only, with reference to the enclosed figures of drawing, wherein.

DETAILED DESCRIPTION OF THE INVENTION

Figure 1:
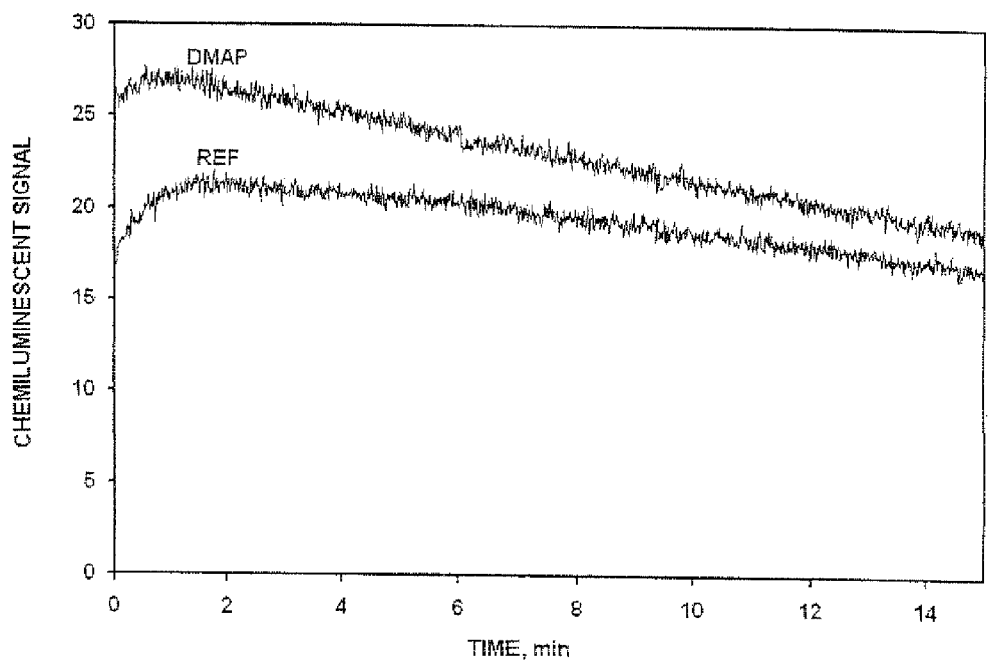
FIG. 1 shows a graph of the chemiluminecsnet signal as a function of time in presence of N-dimethylaminopyridine (DMAP)

The search for nucleophilic acylation catalysts, capable of facilitating the attack of peroxide ion on the carbonylic carbon (C=O) of luminol, and thus increasing the production of light by the chemiluminescent reaction has led to the identification of a group of compounds with the necessary requirements. These compounds, known as hypernucleophilic acylation catalysts or HNAC, see e.g. E. F. V. Scriven, "4-Dialkylaminopyridines: Super Acylation and Alkylation Catalysts", Chem. Soc. Rev. 1983, 12:129-161, do, in fact, possess the characteristic of increasing very significantly the light output produced by the chemiluminescent oxidation of luminol catalyzed by peroxidase and in the presence of electron mediators (electroactive enhancers). Moreover, the compounds found do not act like electroactive enhancers. When using the compounds object of this invention instead of electroactive enhancers, there is in fact no intensification of light output from the oxidation of luminol catalyzed by peroxidase.

From a structural point of view, the compounds of this invention belong to the category of 4-aminopyridines. (A. Hassner, L. R. Krepski, V. Alexanian, Aminopyridines as Acylation Catalysts for Tertiary Alcohols, Tetrahedron 1978, 34:2069-2076; G. Hoefle, W. And Steglich, H. Vorbrueggen, "4-Dialkylaminopyridines as Highly Active Acylation Catalysts", Angew. Chem. Int. Ed. Engl. 1978; 17:569-583.

The hypernucleophilic acylation catalysts (HNACs) of this invention, represented by the general formulas (I) and (II), include in particular 4-diethylaminopyridine, 4-dimethylaminopyridine (DMAP), 4-pyrrolidinopyridine (PPY), 4-piperidinopyridine, 4-(4-methylpiperidin-1-yl)pyridine (MPP), 4-morpholinopyridine (MORP), 4-(2,5-dimethyl-2,5-dihydro-1H-pyrrol-1-yl)pyridine, N,N-dimethyl-N'-pyridin-4-ylimidoformamide and N,N,N',N'-tetramethyl-N"-pyridin-4-yl-guanidine.

Especially preferred are MORP, PPY, DMAP and MPP. These compounds are particularly useful in chemiluminescent assays that require a high level of light output, such as blotting assays, including Western, Southern and Northern blots, as well as dot blot and nucleic acid hybridisation assays. The concentration of hypernucleophilic acylation catalyst is generally in the interval between 0.001 and 20 mmol/liter, preferably between 0.1 mmol and 10 mmol/liter.

The best results are obtained at high pH values, especially in the pH range between 8.9 and 9.4. This interval is significantly higher than the optimum pH range observed in the presence of enhancer, but in the absence of hypernucleophilic acylation catalyst, which is usually between 8.4 and 8.6.

The luminol used must be of a purity suitable and appropriate for luminescence assays. Luminol can be used as the sodium salt. If the analyte to be determined is peroxidase, the concentration of luminol is generally between 0.1 mmol/liter and 50 mmol/liter, preferably between 0.5 and 10 mmol/liter. The oxidant can be any substance capable of oxidizing luminol with emission of light. A source peroxide is preferred, such as hydrogen peroxide or sodium perborate. The concentration of oxidant used in chemiluminescent assays of peroxidase is between 0.1 and 100 mmol/liter, preferably between 0.5 and 10 mmol/liter.

The peroxidase enzyme is normally horseradish peroxidase (HRP) of a quality suitable for use in luminescence assays. Preferably the HRP enzyme is a basic isoenzyme, for example Sigma type VIA or IX. It can be free or conjugated to a ligand.

The electron mediator (electroactive enhancer) can be any electroactive substance able to act as a electron mediator between the oxidant and luminol. In particular, enhancers belonging to the following classes of compounds can be used: benzothiazoles, phenols, aromatic amines, N-alkyl phenothiazines, indophenols, arylboronic acids. The preferred electron mediators are: p-iodophenol, acid p-iodophenylboronic acid, salts of 3-(phenothiazin-10-yl)propane-1-sulfonic acid or 4-(phenothiazin-10-yl)butane-1-sulfonic acid. The electron mediator must be of a purity adequate and appropriate for use in luminescence assays. In particular, it must not contain impurities that can inhibit the chemiluminescent reaction. The concentration of electron mediator used in chemiluminescent assays of peroxidase is between 0.001 and 20 mmol/liter, preferably between 0.1 and 10 mmol/liter.

Chemiluminescent reactions of this invention are applicable to the detection and quantification of analytes using for example the formation of a bond between a protein or nucleic acid and a membrane and peroxidase as tracer. The luminescent reaction is initiated by adding to the membrane a substrate comprising luminol, a source of peroxide, an electron mediator and a nucleophilic acylation catalyst. The emission of light is prolonged and can be measured by film, CDD camera or other instrumentation.

The chemiluminescent assays based on the substrate solutions of this invention include Dot Blot and Western Blot assays for proteins and Southern and Northern Blots assays for nucleic acids. Another important application of the chemiluminescent substrate of the present invention is in ELISA immunoenzymatic assays, especially for analytes present in extremely small quantities, such as tumour markers, thyroid hormones, proteins viruses (HIV, HCV).

EXAMPLES

The following examples serve to illustrate specific aspects of the invention. However, they are not intended to limit the invention.

All the reagents used within the present application have been purchased by Sigma-Aldrich.

Example 1

Effect of N-dimethylaminopyridine (DMAP) on the Chemiluminescent Emission Catalysed by Peroxidase in the Luminol/p-iodophenol System All measurements reported were made with a Varian Eclipse spectrofluorimeter, Bio/Chemiluminescence mode (wavelength emission: 425 nm; emission slit: 20 nm). A chemiluminescent substrate is prepared as follows, comprising:
  3 mM luminol, sodium salt
  2 mM p-iodophenol (electron mediator)
  4 mM sodium perborate
  5 mM 4-dimethylaminopyridine (HNAC)
  0.15 M, pH 9.0 Tris Buffer In addition, a control substrate is prepared, with the same composition as the previous one, but without 4-dimethylaminopyridine (DMAP). Later, to polymethylmethacrylate cuvette containing 2 mL of substrate solution, are added 10 µL of a 0.5 µg/mL horseradish peroxidase (HRP-Type VIA) solution. The solution is mixed for a few seconds with a vortex and measurement of the luminescent signal is carried out for a period of 10 min. The results obtained are shown in FIG. 1. As it can be seen, the substrate containing the hypernucleophilic acylation catalyst DMAP produces a significantly higher signal than the control substrate, which is devoid of it.

Example 2

Effect of Hypernucleophilic Acylation Catalysts on the Chemiluminescent Emission of Luminol All measurements reported were made with a Varian Eclipse spectrofluorimeter, Bio/Chemiluminescence mode (wavelength emission: 425 nm; emission slit: 5 nm). The following chemiluminescent substrates are prepared as follows, comprising:
  5 mM luminol, sodium salt
  3 mM sodium 3-(phenothiazin-10-yl)propane-1-sulfonate
  4 mM sodium perborate (oxidiser)
  Hypernucleophilic Acylation Catalyst (HNAC):
  Substrate A, none;
  Substrate B, 3 mM 4-pyrrolidinopyridine (PPY)
  Substrate C, 3 mM 4-dimethylaminopyridine (DMAP)
  Substrate D, 3 mM 4-morpholinopyridine (MORP)
  0.15 M, pH 9.0 Tris Buffer.

Figure 2:
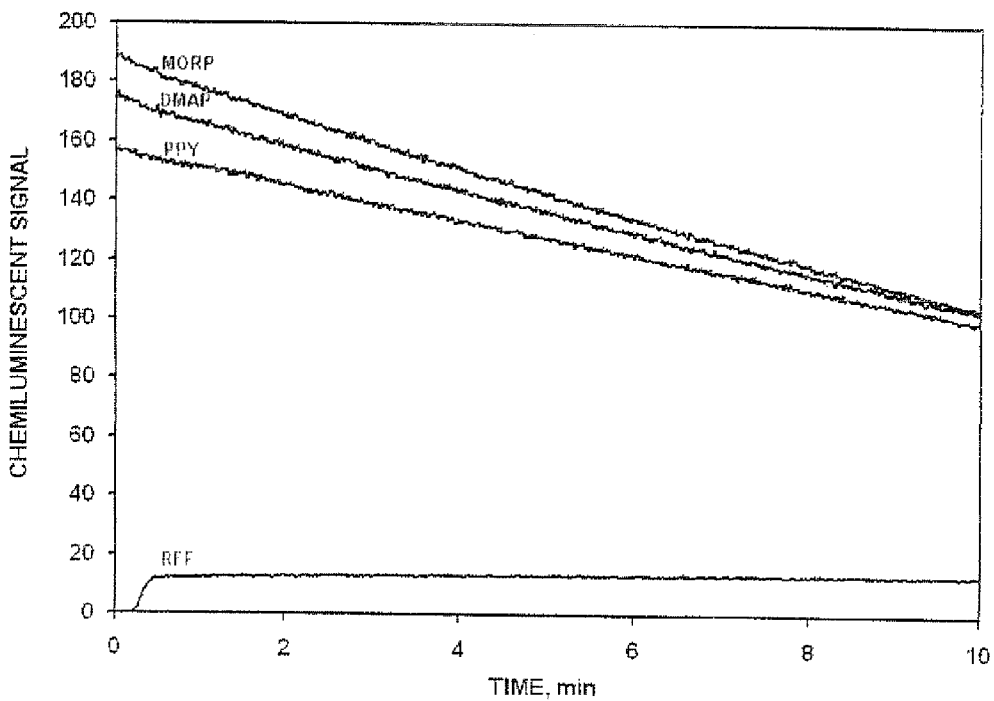
FIG. 2 shown a graph of the chemiluminecsnet signal as a function of time in presence of different hypernucleophilic acylation catalysts according to the instant invention.

Then, a series of polymethylmethacrylate cuvettes is prepared, each containing 2 mL of a substrate solution. To each cuvette are added 10 µL of a 0.5 µg/mL horseradish peroxidase (HRP-Type VIA) solution. The solution is mixed for a few seconds with a vortex and measurement of the luminescent signal is carried out for a period of 10 min. The results obtained are shown in FIG. 2. As it can be seen, during this time period the chemiluminescent signal generated by substrates containing HNAC (Substrates B, C, and D) is from 6 to 12 times more intense compared to Substrate A, which is free of it.

Figure 3:
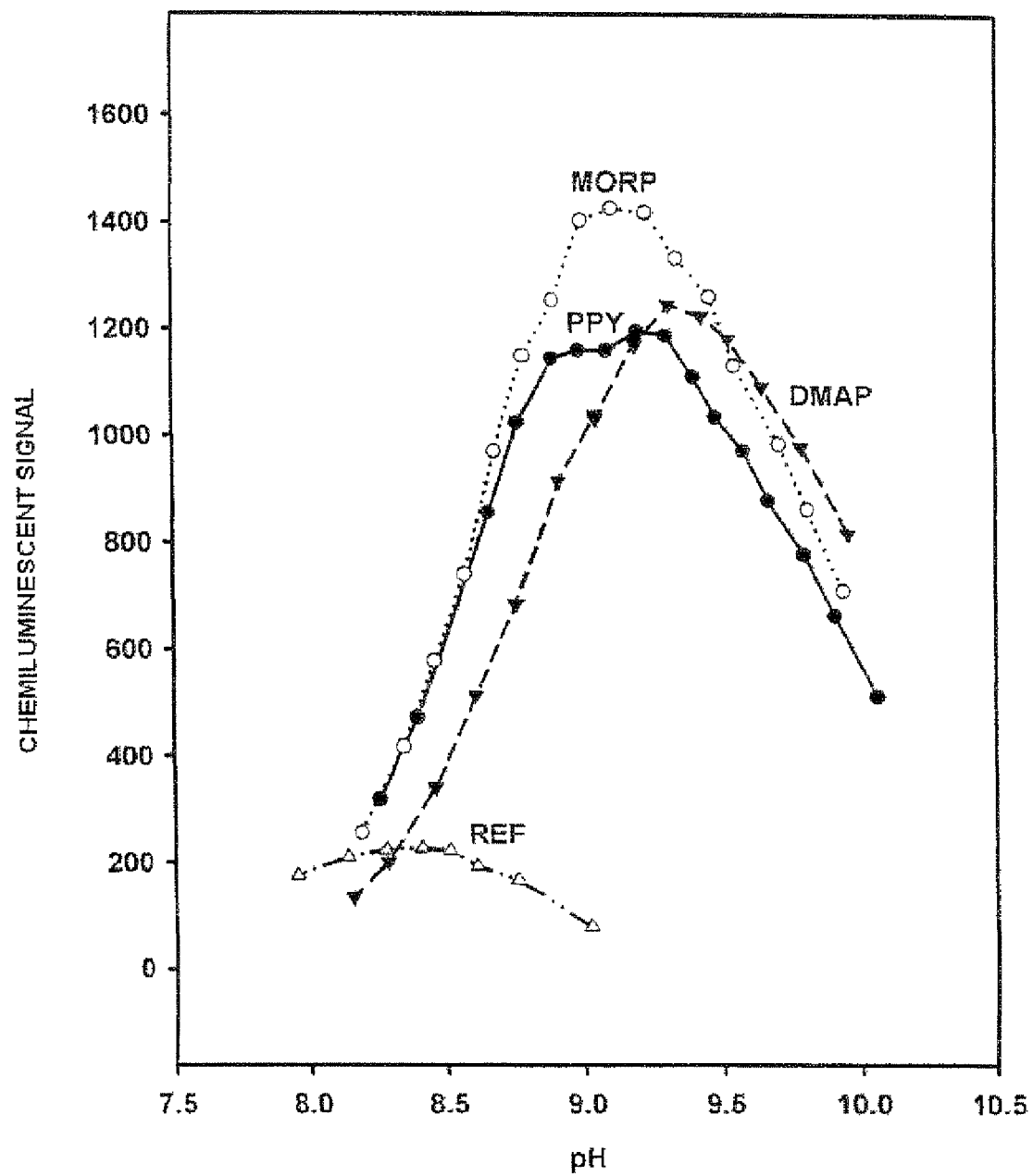
FIG. 3 shows a graph of the chemiluminecsnet signal as a function of pH in presence of different hypernucleophilic acylation catalysts according to the instant invention.

Example 3 pH Dependence of the Effect of HNACs (MORP, DMAP, PPY) on the Chemiluminescent Emission of Luminol The measurements were carried out with a Varian Eclipse spectrofluorimeter, Bio/Chemiluminescence mode (wavelength emission: 425 nm; emission slit: 5 nm; emission filter: open; photomultiplier voltage: medium). Four solutions are prepared with the following composition:
- 5.0 mM sodium luminol
- 4.0 mM sodium perborate
- 3.0 mM sodium 3-(phenothiazin-10-yl)propane-1-sulfonate
- 3.0 mM HNAC (DMAP, MORP o PPY)
- 0.15 M, pH 9.2 Tris Buffer Then, a series of polymethylmethacrylate cuvettes is prepared, each containing 2 mL of a substrate solution. To each cuvette are added small amounts of 5 M HCl or 5 M NaOH, in order to adjust the pH in 8.0-10.0 range without producing in any case significant changes in the total volume. To each cuvette are added 10 μL of a 0.5 μg/mL horseradish peroxidase (HRP-Type VIA) solution. The solution is mixed for a few seconds with a vortex and measurement of the luminescent signal is carried out. For each reaction, the integrated light signal intensity is recorded for the first 600 sec. From the results obtained, which are shown in FIG. 3, it can be seen that in all cases the chemiluminescent signal reaches the maximum value between pH 8.9 and pH 9.4. In the absence of HNAC the optimum signal is obtained in pH range between 8.4 and 8.6. This difference in behaviour can be attributed to the higher concentration of non-protonated HNAC (hypernucleophilic species) in the substrate at higher-pH values (The $pK_a$ of MORP, DMAP and PPY is 8.8, 9.7 e 9.9, respectively).

Example 4

Substrate for Measuring Peroxidase by Chemiluminescence

A Working Solution (Chemiluminescence Substrate) for the measurement of peroxidase can be obtained by mixing equal parts of the following solutions:
Solution A:
- 10 mM luminol, sodium salt
- 6 mM sodio 3-(phenothiazin-10-yl)propane-1-sulfonate
- 3 mM HNAC (hypernucleophilic acylation catalyst)
- 0.3 M Tris Buffer, pH 9.2-9.8 (see note)

Solution B:
- 8 mM sodium perborate
- 50 mM, pH 5.0 acetate buffer

Therefore the Working Solution (Chemiluminescence Substrate) contains:
- 5.0 mM luminol, sodium salt
- 3.0 mM sodium 3-(phenothiazin-10-yl)propane-1-sulfonate
- 3.0 mM HNAC (hypernucleophilic acylation catalyst)
- 4.0 mM sodium perborate.

The pH of the 0.3 M Tris Buffer of Solution A can be adjusted so that the pH of the Working Solution is between 8.6 and 9.4.

Example 5

Limit of Detection of Peroxidase

On a sheet of nitrocellulose membrane commonly used for Western Blot Assays, cut to approximately 2.5×5.0 cm, a series of spots was created with 2 μL solutions containing different concentrations of Horseradish Peroxidase (HRP Type VI-A) in 0.1 M, pH 7.4 Tris buffer additioned with BSA (bovine serum albumin). Each spot was repeated three times, thus creating a 3×7 spot matrix on the membrane. The membrane was air dried and then washed twice with 0.1 M, pH 7.4 Tris buffer. Once dry, the membrane was placed on a microscope slide and inserted into a NightOwl (Berthold Technologies) imaging instrument. A Working Solution was then prepared by mixing:
- 500 μL of solution A prepared as in Example 4 e using 4-morpholinopyridine (MORP) as HNAC (hypernucleophilic acylation catalyst).
- 500 μL di solution B prepared as in Example 4 with which the membrane was soaked. After 5 minutes, the signal was integrated for 300 sec; 10 sec readings were carried out every 5 minutes for half an hour. The data obtained are shown in the following Table:

| Row No. | Horseradish Peroxidase | Signal Intensity (3 spot average) |
| --- | --- | --- |
| 1 | 19 | 3236 |
| 2 | 16 | 2804 |
| 3 | 12 | 2377 |
| 4 | 9 | 1309 |
| 5 | 6 | 718 |
| 6 | 3 | 350 |
| 7 | 0 | 198 |

Figure 4:
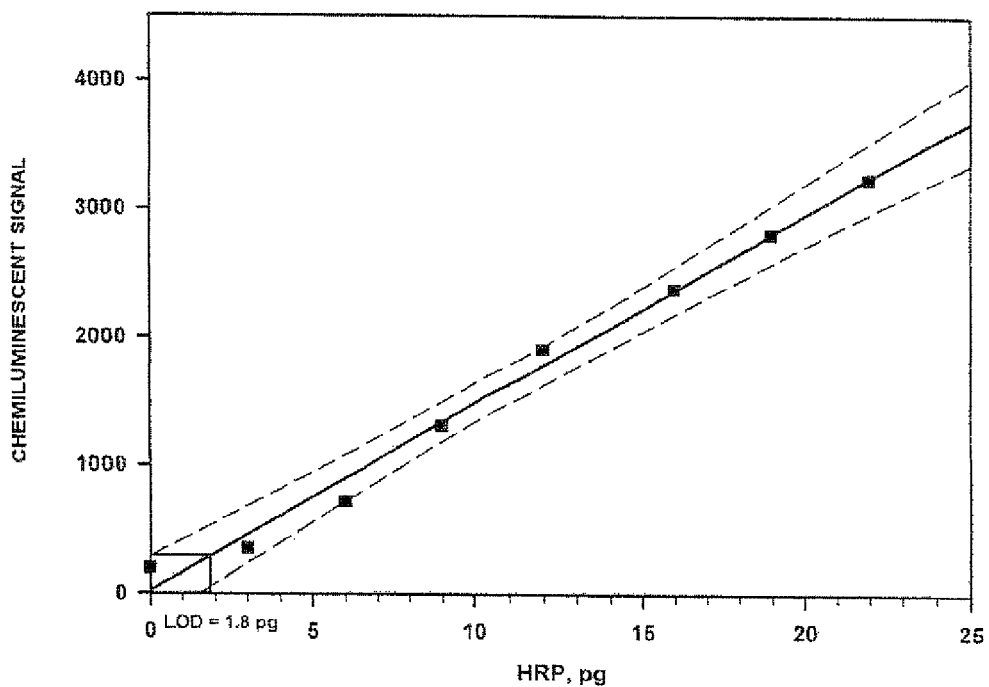
FIG. 4 shows a graph of the chemiluminecsnet signal as a function of the amount of horseradish peroxidase in presence of 4-morpholinopyridine (MORP)

The corresponding data are plotted in a graph, FIG. 4, from which a limit of detection (LOD) for Horseradish Peroxidase (HRP, molecular mass=44,000 daltons) of 1.8 pg (41 amol) is obtained. On the other hand, using a chemiluminescent substrate prepared as in Example 4, but without HNAC results in a LOD of 10 pg (230 amol). Similarly, the dose-response curve of Horseradish Peroxidase (L. J. Kricka, M. Cooper and Xiaoying Ji, "Synthesis and Characterization of 4-iodophenylboronic Acid: A New Enhancer for the Horseradish Peroxidase Chemiluminescent-Catalyzed Oxidation of Luminol," Anal. Biochem. 1996; 240:119-125) on a luminol-peroxide chemiluminescent substrate enhanced with p-iodophenylboronic but no HNAC results in a LOD of 509 amol. Therefore, the chemiluminescent substrate prepared as described in Example 4 and containing HNAC, allows the determination of Horseradish Peroxidase, with a sensitivity at least 6-12 times higher than the corresponding substrates containing an electron mediator, but without HNAC.

Example 6

Western Blot Assay on Yersinia Enterocolitis Lysate

Figure 5:
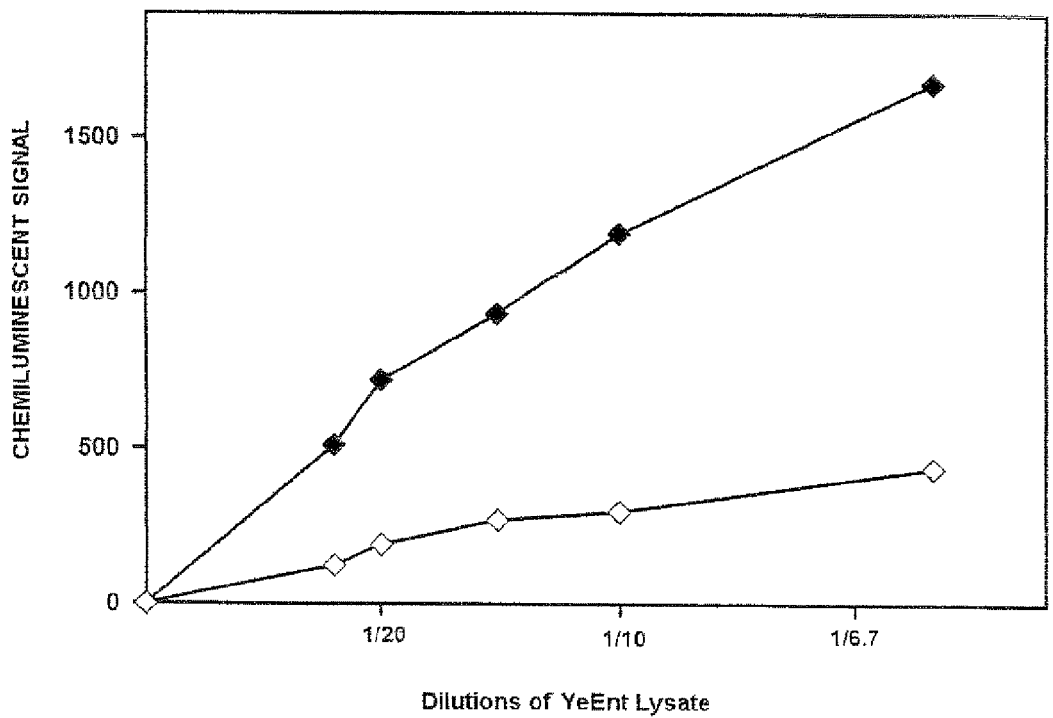
FIG. 5 shows a graph of the chemiluminecsnet signal for the detection of Yersinia Enterocolitis in presence (■) and in absence (□) of HNAC.

The blotting method used is described by H. Towbin et al. Proc. Natl. Acad. Sci. 76, 4350-4353 (1979). Various concentrations of Yersinia Enterocolitis lysate were separated by gel electrophoresis on 12% sodium dodecylsulfate (SDS) polyacrylamide gel. The gel was transferred to a nitrocellulose membrane for Western Blot. Non-specific binding sites were blocked with a 5% milk powder solution for 1 hour and then washed several times with a wash buffer (20 mM Tris, 137 mM NaCl). The blots were then incubated with the primary antibody (rabbit anti-YeEnt, dilution 1:10 000) for one hour, then washed as above to remove the antibody not linked to the antigen. The membrane with the blot was incubated for 1 hour with the secondary antibody labeled with HRP (goat anti-mouse HRP, Sigma A-6154, dilution 1:3000), with subsequent washing. The membrane was cut into two parts. Two Working Solutions were prepared according to Example 4, with HNAC (4-morpholinopyridine) or without HNAC. The Working Solutions were added to the membranes and incubated for five minutes. The chemiluminescent signal o was acquired with an imaging instrument (NightOwl, Berthold Technologies) for 1 minute. FIG. 5 illustrates the intensity of the signal obtained using the two solutions. It is evident that the substrate solution containing HNAC according to this invention shows a brightness and sensitivity considerably higher than the solution lacking HNAC Example 7

α-fetoprotein (AFP) ELISA Assay

Figure 6:
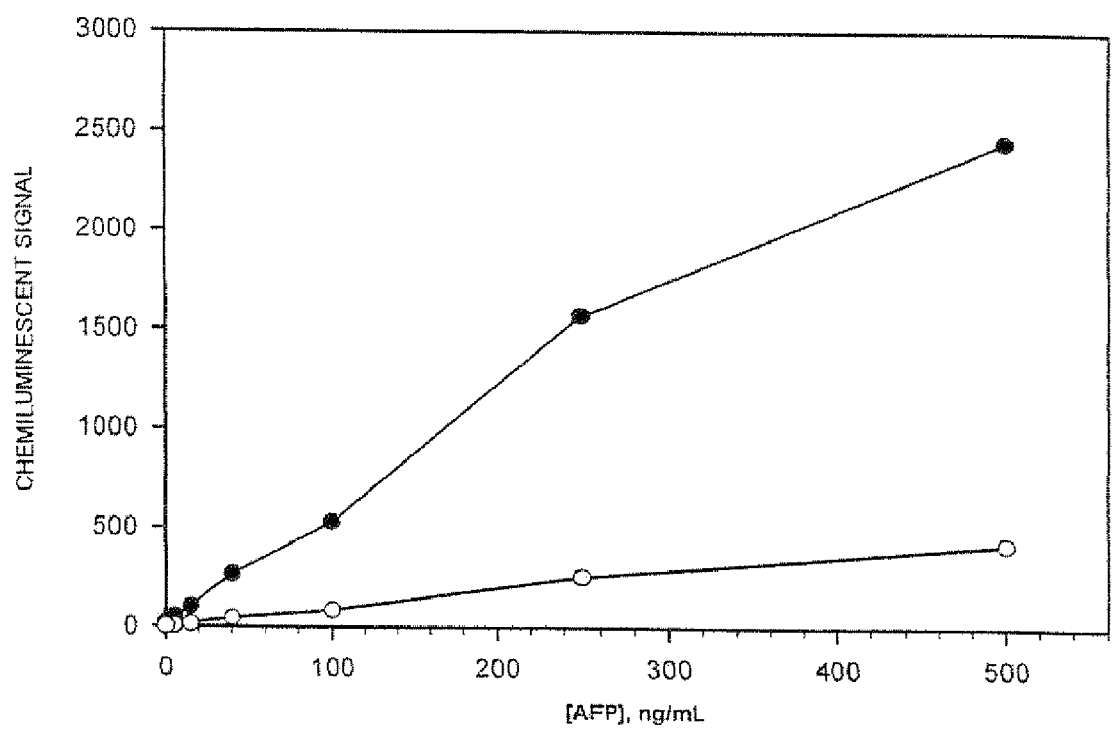
FIG. 6 shows a graph of the chemiluminecsnet signal for the detection of alpha-fetoprotein in presence (•) and in absence (○) of HNAC.

This immunometric assay is based on the immunochemical reaction between a capture antibody, an antigen (α-fetoprotein, AFP), and a HRP-labeled antibody. Wells with capture antibody were prepared by incubating the microwell plates coated with streptavidin with a solution of biotinylated capture antibody. The wells were then incubated with α-fetoprotein (AFP) calibrators from a commercial kit. 25 µL of a AFP calibrator were added to each well. After an incubation period of one hour, the plate was washed with PBS-0.05% Tween-20. 200 µL of a solution of anti-AFP antibody labeled with HRP were then added to each well. The wells were incubated at room temperature for 1 hour and then washed to remove excess conjugate. Two Working Solutions were prepared according to Example 4, with HNAC (4-dimethylaminopyridine) or without HNAC. The Working Solutions were added to the wells and incubated for ten minutes. The chemiluminescent signal was acquired with a plate reader (Luminoskan Ascent, LabSystems) for 1 minute. FIG. 6 shows the dose-response curve for AFP. Again, it is clear that the solution containing HNAC of this invention shows a higher signal and consequently a significantly higher sensitivity compared to the solution that lacks HNAC Naturally, while the principle of the invention remains the same, the details of construction and the embodiments may widely vary with respect to what has been described and illustrated purely by way of example, without departing from the scope of the present invention.

The invention claimed is:

1. A kit for performing an assay comprising luminol, an oxidant, an electron mediator and a hypernucleophilic acylation catalyst.

2. The kit according to claim 1, wherein the hypernucleophilic acylation catalyst (HNAC) is selected from the group of compounds represented by Formula (I):

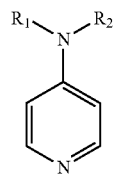

FORMULA (I)

where:
$R_1$ and $R_2$ represent both or each separately, hydrogen, methyl, ethyl, propyl, butyl and isopropyl,
or
$R_1$ and $R_2$ together represent —$(CH_2)_4$— thus forming a pyrrolidone ring with the nitrogen atom,
or
$R_1$ and $R_2$ together represent —$(CH_2)_5$— thus forming a piperidine ring with the nitrogen atom,
or
$R_1$ and $R_2$ together represent —$(CH_2)_2$—$CHCH_3$—$(CH_2)_2$— thus forming a 4-methylpiperidine ring with the nitrogen atom,
or
$R_1$ and $R_2$ together represent —$(CH_2)_2$—O—$(CH_2)_2$— thus forming a morpholine ring with the nitrogen atom,
or
$R_1$ and $R_2$ together represent —$(CHCH_3)$—CH=CH$(CHCH_3)$— thus forming a 2,5-dimethyl-2,5-dihydro-1H-pyrrole ring with the nitrogen atom.

3. The kit according to claim 1, wherein the hypernucleophilic acylation catalyst (HNAC) is selected from the group of compounds represented by Formula (II):

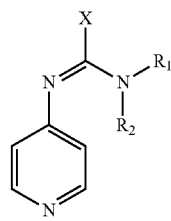

FORMULA (II)

where:
X represents hydrogen, methyl, ethyl, propyl, butyl or isopropyl, while $R_1$ and $R_2$ represent both or each separately, hydrogen, methyl, ethyl, propyl, butyl and isopropyl,
or
X represents $NH_2$, or N(methyl)$_2$, or N(ethyl)$_2$, or N(propyl)$_2$, or N(isopropyl)$_2$, or N(butyl)$_2$, while $R_1$ and $R_2$ represent both or each separately, hydrogen, methyl, ethyl, propyl, isopropyl, or butyl.

4. The kit according to claim 1, wherein the hypernucleophilic acylation catalyst (HNAC) is selected among 4-diethylaminopyridine, 4-dimethylaminopyridine (DMAP), 4-pyrrolidinopyridine (PPY), 4-piperidinopyridine, 4-(4-methylpiperidin-1-yl)pyridine (MPP), 4-morpholinopyridine (MORP), 1a 4-(2,5-dimethyl-2,5-dihydro-1H-pyrrol-1-yl)pyridine, N,N-dimethyl-N'-pyridin-4-ylimidoformamide and N,N,N',N'-tetramethyl-N''-pyridin-4-yl-guanidine.

5. The kit according to claim 1, wherein the oxidant is sodium perborate.

6. The kit according to claim 1, wherein the electron mediator is p-iodophenol.

7. The kit according to claim 1, wherein the electron mediator is sodium 3-(phenothiazin-10-yl)propane-1-sulfonate.

8. The kit according to claim 1, wherein the kit comprises two solutions, wherein the first solution contains luminol, the electron mediator and the hypernucleophilic acylation catalyst, and the second solution contains the oxidant.

9. The kit according to claim 8, wherein the first solution has a pH between 8.0 and 10.

10. The kit according to claim 8, wherein the first solution has a pH between 4.0 and 5.0.

11. The kit according to claim 10 wherein the first solution has a pH between about 4.5 and 5.0.

* * * * *

(12) EX PARTE REEXAMINATION CERTIFICATE (9871st)
United States Patent
Della Ciana

(10) Number: US 8,129,136 C1
(45) Certificate Issued: Oct. 11, 2013

(54) KIT FOR PERFORMING AN ASSAY

(75) Inventor: Leopoldo Della Ciana, Bologna (IT)

(73) Assignee: Cyanagen Srl, Bologna (IT)

Reexamination Request:
No. 90/012,476, Sep. 7, 2012

Reexamination Certificate for:
Patent No.: 8,129,136
Issued: Mar. 6, 2012
Appl. No.: 12/805,827
Filed: Aug. 20, 2010

Related U.S. Application Data

(63) Continuation of application No. 12/071,333, filed on Feb. 20, 2008, now Pat. No. 7,803,573.

(30) Foreign Application Priority Data

Feb. 20, 2007 (IT) .................................. BO07A0112

(51) Int. Cl.
*C12Q 1/28* (2006.01)

(52) U.S. Cl.
USPC ............................................. 435/28; 435/975

(58) Field of Classification Search
None
See application file for complete search history.

(56) References Cited

To view the complete listing of prior art documents cited during the proceeding for Reexamination Control Number 90/012,476, please refer to the USPTO's public Patent Application Information Retrieval (PAIR) system under the Display References tab.

*Primary Examiner* — Gary Kunz

(57) ABSTRACT

The present invention relates to a kit for performing an assay. The kit comprises luminol, an oxidant, an electron mediator and a hypernucleophilic acylation catalyst.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2-4 and 6-8 are cancelled.

Claims 1 and 9-11 are determined to be patentable as amended.

Claim 5, dependent on an amended claim, is determined to be patentable.

1. A kit for performing an assay comprising luminol, an oxidant, [an] *the* electron mediator *sodium 3-(phenothiazin-10-yl)propane-1-sulfonate* and [a hypernucleophilic acylation catalyst] *4-morpholinopyridine (MORP), wherein the kit comprises two solutions, wherein the first solution contains luminol, the electron mediator and MORP, and the second solution contains the oxidant*.

9. The kit according to claim [8] *1*, wherein the first solution has a pH between 8.0 and 10.

10. The kit according to claim [8] *1*, wherein the [first] *second* solution has a pH between 4.0 and 5.0.

11. The kit according to claim 10 wherein the [first] *second* solution has a pH between about 4.5 and 5.0.

* * * * *